United States Patent [19]

Lipshaw

[11] 4,188,246
[45] Feb. 12, 1980

[54] MICROSCOPE SLIDE AND METHOD FOR MAKING SAME

[76] Inventor: Julius Lipshaw, 23040 Valley Crest La., Southfield, Mich. 48034

[21] Appl. No.: 944,579

[22] Filed: Sep. 21, 1978

Related U.S. Application Data

[62] Division of Ser. No. 809,368, Jun. 23, 1977, abandoned.

[51] Int. Cl.² .......................... A01N 1/00; A01N 3/00
[52] U.S. Cl. ...................................... 156/57; 428/15; 428/195
[58] Field of Search ................... 156/57; 428/13, 15, 428/195; 427/2, 165

[56] References Cited

U.S. PATENT DOCUMENTS

| | | | |
|---|---|---|---|
| 3,130,099 | 4/1964 | Homburger | 156/57 |
| 3,737,335 | 6/1973 | Feinberg | 156/57 X |
| 3,770,477 | 11/1973 | Weichselbaum | 156/57 X |
| 3,995,022 | 11/1976 | Heanley et al. | 156/57 X |

*Primary Examiner*—George F. Lesmes
*Assistant Examiner*—Daniel R. Zirker
*Attorney, Agent, or Firm*—Barnes, Kisselle, Raisch & Choate

[57] ABSTRACT

A process for making a microscope side having a specimen hermetically sealed on a transparent slide plate by a transparent coating of a plastic material in solid form. Preferably, the plastic material is applied to a slide plate with a specimen thereon in liquid form and converted to a solid coating of transparent plastic material.

9 Claims, 10 Drawing Figures

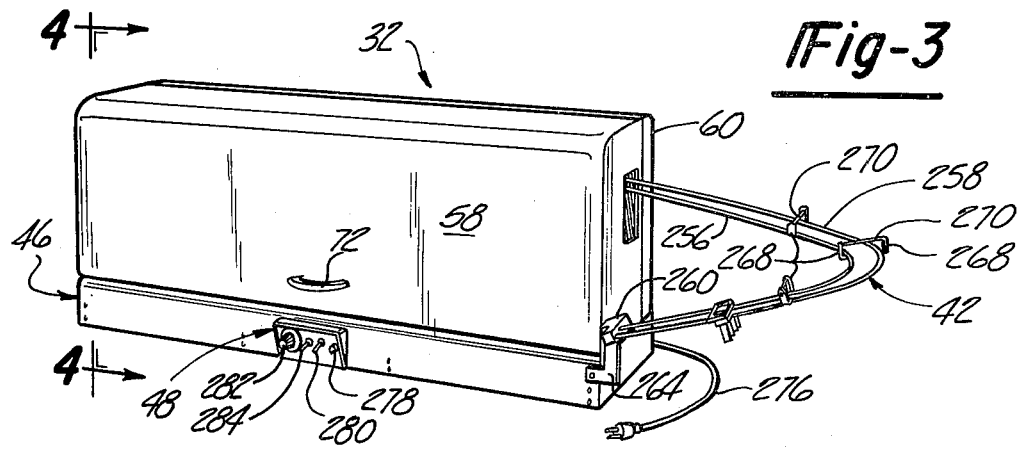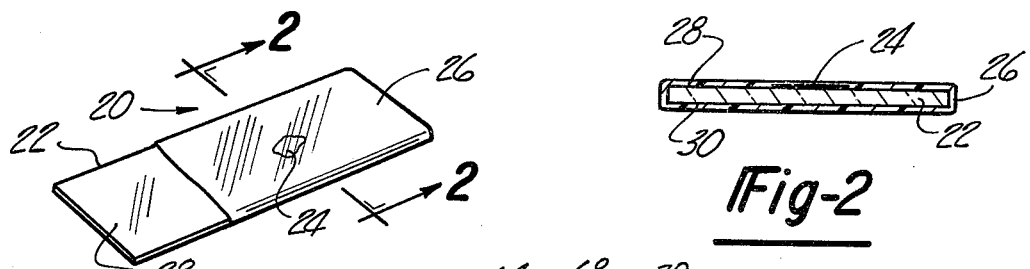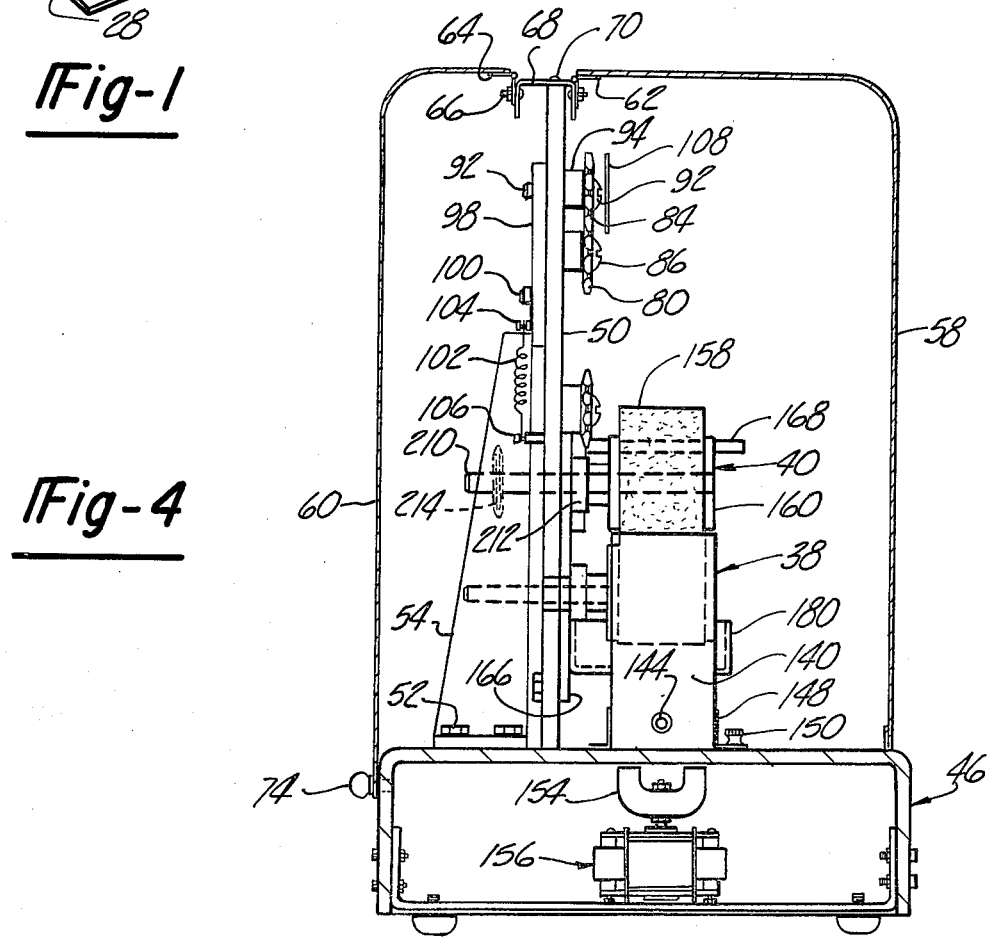

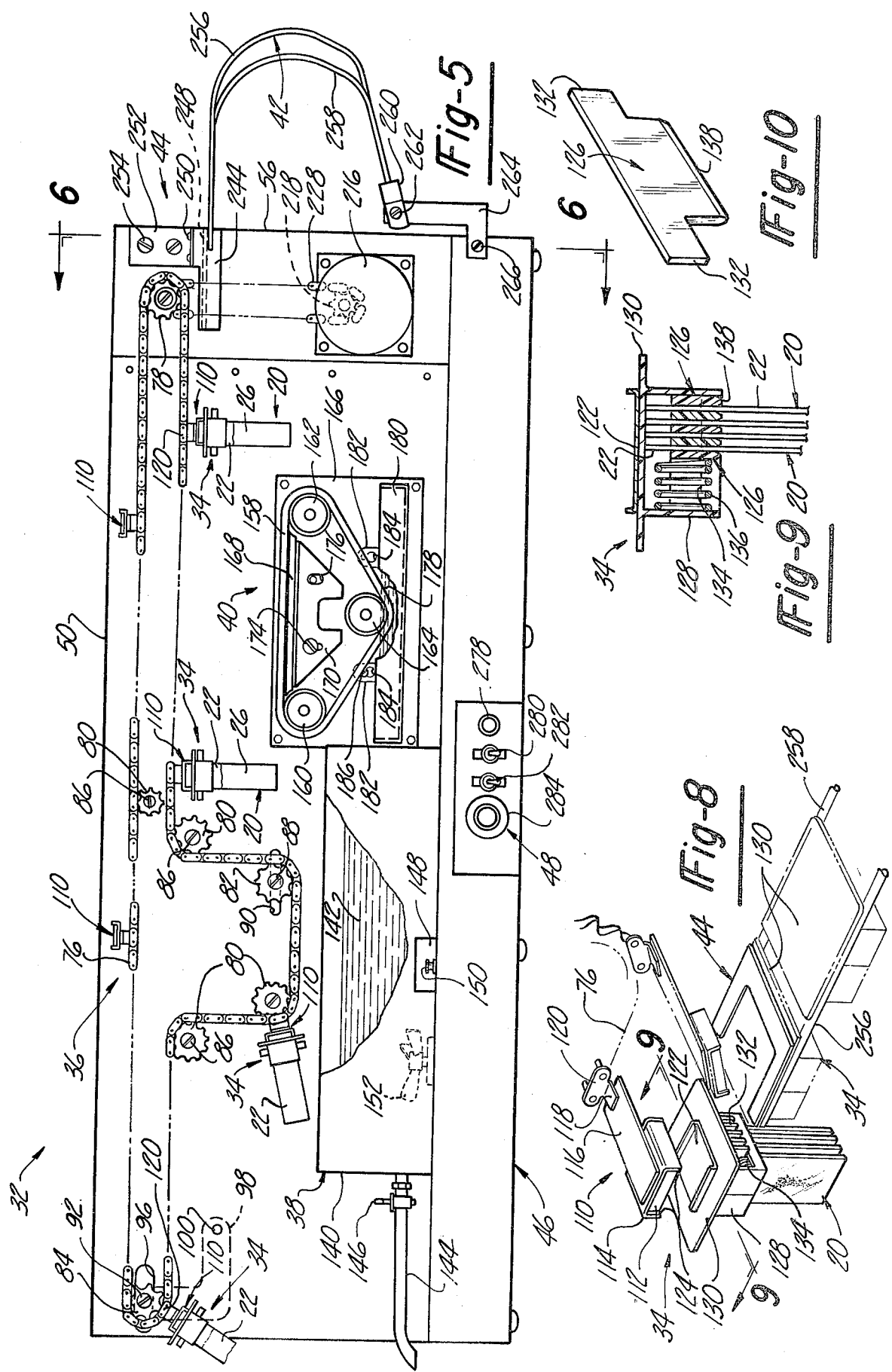

MICROSCOPE SLIDE AND METHOD FOR MAKING SAME

This is a division of application Ser. No. 809,368, filed June 23, 1977, now abandoned. A divisional application, Ser. No. 944,580, dealing with the apparatus claims of the original application has been filed on 9/21/78.

This invention relates to an improved microscope slide and a method for making microscope slides.

Conventional microscope slides are prepared by cleaning a plate of transparent glass, commonly called a slide plate, mounting a specimen such as a histological tissue or various smears on one face of the slide plate, if desired staining the specimen, applying an adhesive to the face of the slide plate having the specimen thereon, and positioning another flat plate of transparent glass commonly called a cover glass over the specimen and in contact with the adhesive to secure the cover glass to the slide plate and thereby provide a complete microscope slide.

Such conventional microscope slides are quite expensive because the cover glass is costly and substantial time of a skilled technician is required to apply and secure the cover glass to the slide plate. Considerable refocusing of a microscope is required when viewing different portions of such a conventional microscope slide and when viewing different conventional microscope slides due to variations in the thickness of the adhesive and differences in the extent to which the faces of the slide plate and the cover glass are skewed or unparallel with each other. Such skewing of the faces of the slide plate and cover glass are usually due to variations in the thickness of the adhesive and the inability of most skilled technicians to consistently secure the cover glass and the glass plate together so that the faces thereof are absolutely parallel to each other.

Microscope slides of this invention have a flat slide plate of a clear and transparent material such as glass with a specimen thereon and a solid coating of a clear and transparent plastic material adhering to the slide plate, overlying at least the specimen, and hermetically sealing the specimen to the slide plate. With the method of this invention such a microscope slide is produced by mounting the specimen on the slide plate, if desired staining the specimen, applying a liquid coating of the plastic material over the specimen, and converting the liquid coating to solid form. Preferably any excess liquid coating applied to the slide plate is removed therefrom before converting the coating to solid form.

An apparatus applies the liquid coating to the slide plate with the specimen thereon by dipping the slide plate into and out of a tank containing a liquid mixture of the plastic material, and removes any excess liquid coating of plastic material from the slide plate by permitting any excess liquid coating to accumulate adjacent to a lower edge of the slide plate and then contacting such lower edge with an absorbent material to remove any excess coating. Preferably the liquid coating is applied and any excess coating removed while the slide plate is suspended in a generally vertical plane. Preferably the apparatus saturates the absorbent material with a solvent of the plastic material to facilitate removal of any excess liquid coating from the lower edge of the slide plate.

Objects, features, and advantages of the microscope slide and process of this invention are the elimination of costly cover glass; decreasing the amount of refocusing required to view different portions of the same microscope slide and different microscope slides; preventing discoloration and/or deterioration of specimens, even if stored for many years, by hermetically sealing each specimen to a slide plate; substantially decreasing the time and effort required by a skilled technician to prepare a microscope slide; and improved economy, ease and reliability in preparing microscope slides.

These and other objects, features, and advantages of this invention will be apparent from the following detailed specification, appended claims, and accompanying drawings in which:

FIG. 1 is a perspective view of a microscope slide of this invention.

FIG. 2 is a sectional view on line 2—2 of FIG. 1.

FIG. 3 is a perspective view of an apparatus for making a microscope slide in accordance with the process of this invention.

FIG. 4 is a sectional view on line 4—4 of FIG. 3 adjacent one end of the apparatus.

FIG. 5 is a front view with the cover removed and portions broken away of the apparatus of FIG. 3.

FIG. 8 is a fragmentary perspective view of a microscope slide carrier and a carrier pickup and transfer mechanism of the apparatus of FIG. 3.

FIG. 9 is a fragmentary sectional view on line 9—9 of FIG. 8.

FIG. 10 is a perspective view of a leaf of the microscope slide carrier of FIG. 8.

Figure 6:
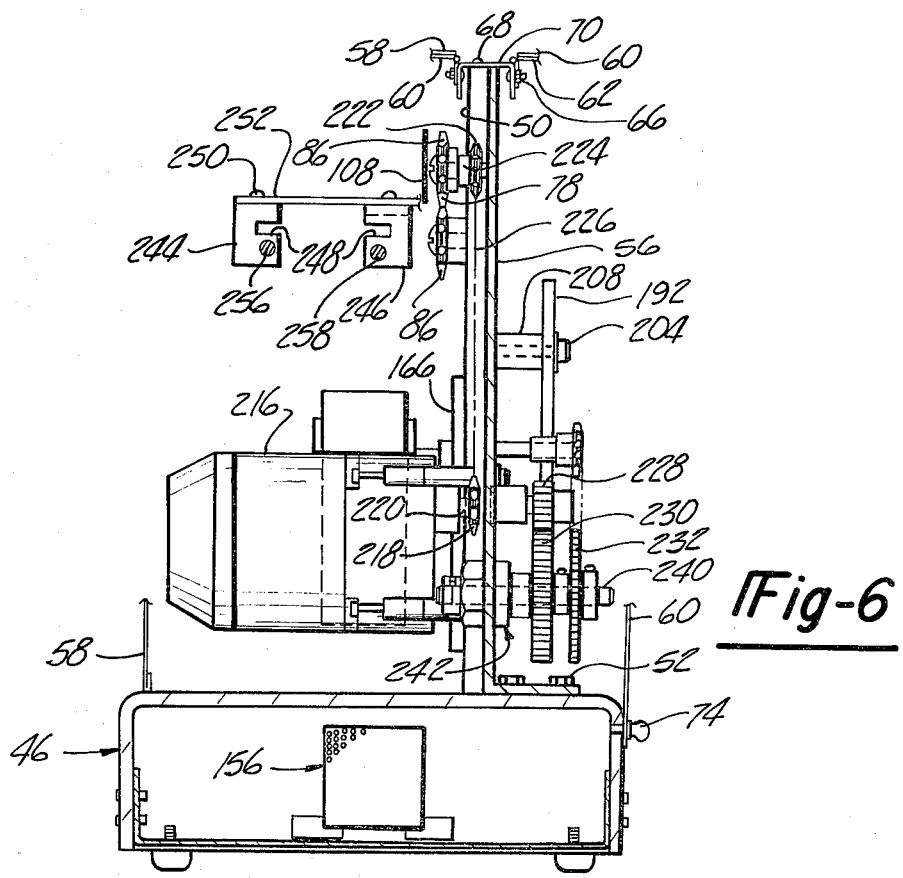
FIG. 6 is a view of the other end of the apparatus of FIG. 3 with portions broken away.

Referring in more detail to the drawings, FIGS. 1 and 2 illustrate a microscope slide 20 of this invention having a slide plate 22 with a specimen 24 mounted thereon and covered by a coating 26 of a plastic material which hermetically seals specimen 24 to plate 22. Slide plate 22 is of substantially uniform thickness, has two substantially parallel and flat faces 28 and 30, and is made of a solid transparent and preferably clear material such as glass or plastic.

At least the exterior surface of at least the portion of the coating 26 overlying specimen 24 is substantially flat and none of the exterior surface of the portion of the coating overlying face 28 of the plate projects beyond the plane of the portion of the exterior surface of the coating overlying specimen 24. Preferably the entire exterior surface of the portions of coating 26 overlying face 28 and face 30 of the plate are each substantially flat and each lie in a single plane with the planes being substantially parallel to each other. Coating 26 is a solid transparent and preferably clear plastic material which adheres to plate 22 such as a transparent synthetic enamel.

In accordance with the method of this invention, microscope slide 20 is made by mounting or otherwise applying a specimen 24 to one face of a clean slide plate 22, if desired staining the specimen, and applying a coating 26 of transparent plastic material to the plate over at least the specimen so that the plastic material adheres to the plate and hermetically seals the specimen thereon. Preferably coating 26 is applied to plate 22 in liquid form and then converted to solid form such as by dipping the plate with the specimen thereon into a liquid mixture of a plastic material and an organic solvent and then after removing the plate from the mixture, and preferably after removing any excess liquid coating from the plate, converting the liquid coating on the plate into solid form by evaporating at least a portion of the solvent in the liquid coating on the plate. Preferably plate 22 is positioned in a generally vertical plane when applying the liquid coating to plate 22, removing any excess liquid coating therefrom, and converting the liquid coating into a solid coating 26 of plastic material. By suspending the plate 22 in a vertical position for a short period of time immediately after it has been removed from the mixture, any excess liquid coating will flow by gravity toward and accumulate adjacent the lowermost edge of the plate. Any such accumulation of excess liquid coating may be removed from the plate by contacting the lower edge of the plate with an absorbent material which is preferably saturated with a solvent of the plastic material to facilitate absorption of any such accumulated excess liquid coating.

Figure 7:
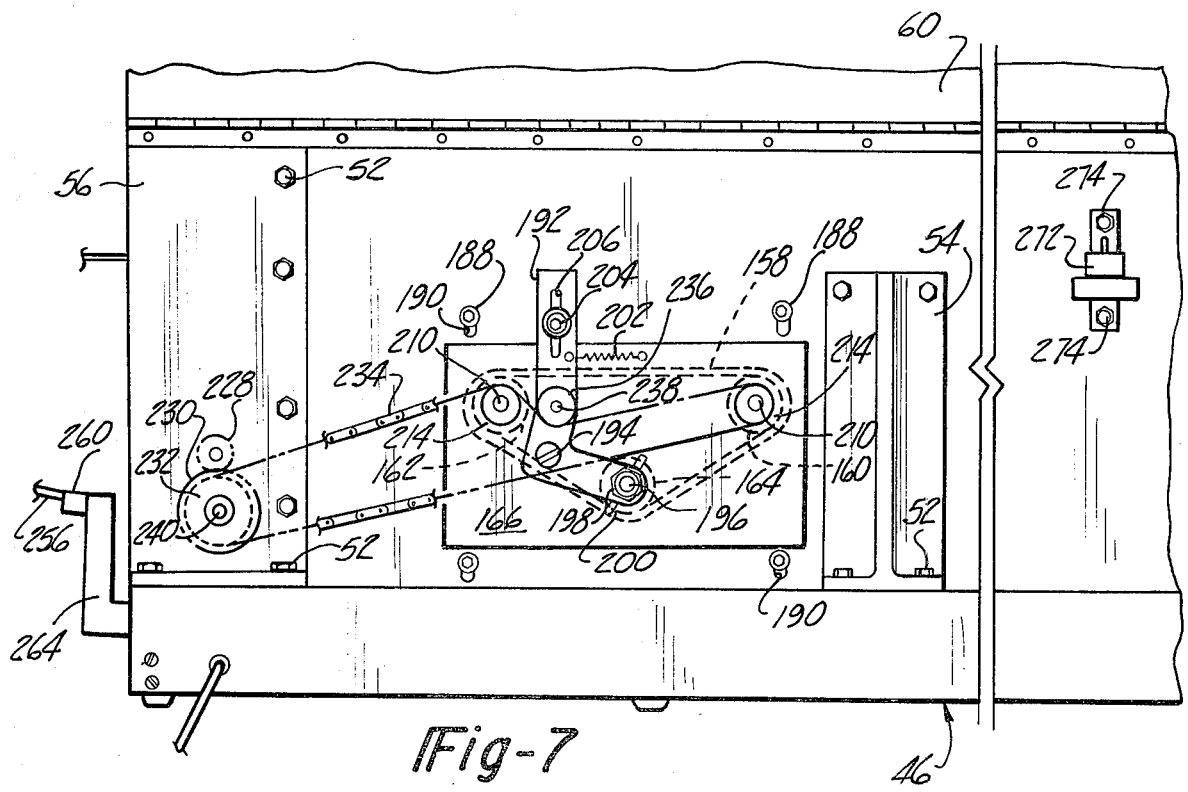
FIG. 7 is a fragmentary rear view of the apparatus of FIG. 1.

FIGS. 3–8 illustrate an apparatus or machine 32 for making microscope slides 20 in accordance with the process of this invention. As shown in FIG. 5, in machine 32, slide plates 22 are releasably retained in slide carriers 34 and moved by a conveyor assembly 36 through a dip tank assembly 38, across an absorber assembly 40, and onto a storage and drying rack 42 by cooperation with a pickup and transfer mechanism 44. Machine 32 has a base 46 with a control panel 48 on the front thereof and an upstanding mounting panel 50 secured to the base by fasteners 52 and right angle brackets 54 and 56 (FIG. 7). As shown in FIGS. 3 and 4, machine 32 has a front cover 58 and a rear service panel 60 connected by piano hinges 62 and 64 and fasteners 66 to a filler panel 68 secured by cap screws 70 to the top of mounting panel 50. Front cover 58 has a handle 72 thereon and when swung fully open to permit operation of machine 32, rests on the top of service panel 60. Service panel 60 is normally secured in its closed position to base 46 of machine 32 by thumb screws 74.

As shown in FIG. 5, conveyor assembly 36 has a closed loop of chain 76 received on and positioned by a driven sprocket 78 and a plurality of idler sprockets 80, 82 and 84. Idler sprockets 80 are mounted for rotation on screws 86 fixedly secured to mounting panel 50. To permit variation of the distance through which conveyor 36 traverses slide plates 22 through dip tank assembly 38, idler sprocket 82 is mounted for rotation on a screw 88 extending through a slot 90 in panel 50 which permits the sprocket to be secured to the panel in a variety of positions.

To both take up slack in and permit adjustment of the tension of chain 76, idler sprocket 84 is mounted for rotation on a screw 92 which extends through both a spacer 94 (FIG. 4) and a slot 96 in panel 50 and is threaded into a dog leg lever 98 adjacent one end thereof. Dog leg lever 98 is pivotally mounted adjacent its other end on the back face of panel 50 by a cap screw 100. The desired tensioning force on chain 76 is applied through dog leg lever 98 by a tension spring 102 connected at one end to a pin 104 fixed to the central portion of lever 98 and at the other end to a pin 106 fixed to panel 50. Loosening screw 92 permits lever 98 to pivot freely and apply to chain 76 the tensioning force produced by spring 102, and retightening of screw 92 secures idler sprocket 84 on panel 50 in the position determined by the force of the tensioning spring so that sprocket 84 remains in a fixed position on the panel during normal operation of conveyor assembly 36. To prevent injury, a protective guard 108 (FIGS. 4 and 6 only) overlies chain 76 and all the sprockets of the conveyor assembly 36, and is releasably secured to panel 50.

As shown in FIGS. 5 and 8, slide carriers 34 are releasably connected to conveyor assembly 36 by magnetic holders 110 each having a permanent magnet 112 received in a steel bracket 114 fixed to one end of a cantilever arm 116 the other end of which is fixed to a tab 118 of a link 120 of chain 76 of the conveyor assembly. Each side carrier 34 is releasably retained on magnetic holder 110 by the attraction of magnet 112 for a steel U shaped bracket 122 fixed to each slide carrier. Each slide carrier 34 is oriented with respect to magnetic holder 110 by the upstanding legs of bracket 122 being constructed and arranged so that they can only be received in recesses 124 defined by magnet 112 and bracket 114 of each holder 110.

As shown in FIGS. 8–10, each slide carrier 34 is constructed and arranged to releasably retain a plurality of slides 20 by engaging and frictionally retaining the upper portion of a slide plate 22 between a pair of leaves 126 slidably carried by a generally rectangular frame 128 fixed to a base plate 130 to which bracket 122 is secured. To mount and facilitate manually moving the leaves, each leaf 126 has a pair of opposed tabs 132 slidably received in and extending outwardly beyond a pair of slots 134 in frame 128. Leaves 126 are yieldably urged towards each other and into engagement with any slide plates 22 received therebetween by a compression spring 136 received between one end of frame 128 and the leaves. To facilitate insertion of slide plates 22 between leaves 126, each leaf has a tapered leading edge 138.

As shown in FIG. 5, dip tank assembly 38 has a general rectangular tank 140 with an open top for holding a quantity of liquid plastic material 142 for producing coating 26. Tank 140 has a drain tube 144 with a valve 146 extending from one end, and is releasably secured by a bracket 148 and a knurled screw 150 to base 46. A propeller 152 of a conventional magnetic stirrer is mounted for rotation in the bottom of tank 140 and is driven through a magnetic coupling 154 by an electric motor 156 (FIG. 4) mounted in the bottom of base 46.

Absorber assembly 40 has a continuous belt 158 of an absorbent material such as cotton received over two driven spools 160 and 162 and an idler spool 164 mounted for rotation on a carrier plate 166. A portion of belt 158 extending between driven spools 160 and 162 is supported by an underlying flat plate 168 fixed to a vertically adjustable mounting bracket 170 secured to carrier plate 166 by a pair of screws 174 (only one of which is shown) extending through elongate slots 176 and threaded into the carrier plate. In operation of machine 32, belt 158 is saturated with a solvent 178 for the liquid plastic material 142, solvent 178 preferably being an aromatic solvent such as xylene or toluene, by being partially submerged in the solvent which is received in a bath tray 180 with an open top. Tray 180 is removably mounted on carrier plate 166 by the cooperation of a pair of mounting tabs 182 having a bulbous opening 184 therethrough slidably engageable with pins 186 with enlarged heads and reduced shanks fixed to carrier plate 166. To permit absorber assembly 40 to be adjusted vertically so that the upper surface of belt 158 will contact the lower edge of slide plates 22, carrier plate 166 is releasably secured to mounting panel 50 by cap scress 188 extending through slots 190 (FIG. 7) in panel 50 and threaded into the carrier plate.

As shown in FIG. 7, belt 158 is placed in tension by an idler arm 192 pivotally mounted by a screw 194 on carrier plate 166 and having a shaft 196 secured by a nut 198 to one end of the arm and extending through an elongate slot 200 in the carrier plate with idler spool 164 mounted for rotation thereon. A tensioning force is applied through arm 192 and spool 164 to belt 158 by spring 202 connected at one end to a pin fixed to plate 166 and at the other end to a pin fixed to the idler arm. Idler arm 192 is releasably locked in adjusted position by a cap screw 204 which extends through a slot 206 in the arm and a spacer 208, and is threaded into panel 50. Driven spools 160 and 62 are each fixed to a shaft 210 journaled for rotation in a bushing 212 (FIG. 4) received in plate 166 and having a sprocket 214 fixed to one end of the shaft.

As shown in FIGS. 5–7, an electric motor 216 simultaneously drives both conveyor assembly 36 and absorber assembly 40 in unison so that absorber belt 158 and an overlying portion of conveyor chain 46 travel in the same direction at the same speed so that there is no relative movement between the lower edge of a slide plate 22 and the portion of belt 158 contacted by the lower edge of the slide plate. As shown in FIG. 6, motor 216 drives conveyor assembly 36 through a sprocket 218 fixed to the drive shaft 220 of the motor, a sprocket 222 carried by screw 86 and coupled through collar 224 with sprocket 78 for rotation therewith, and a drive chain 226 received on sprockets 218 and 222. Motor 216 also drives absorber assembly 40 through a spur drive gear 228 fixed to shaft 220, a spur reducer gear 230, and a drive sprocket 232 connected by a chain 234 to both driven sprockets 214 and retained in engagement therewith by an idler sprocket 236 mounted for rotation on a shaft 238 fixed to idler lever 192. Idler sprocket 236 in cooperation with arm 192 permits adjustment of the tension in chain 234 simultaneously with the adjustment of the tension in belt 158. Spur reducer gear 230 and drive sprocket 232 are both fixed to a stub shaft 240 mounted for free rotation in a bearing assembly 242 secured to motor mounting bracket 58.

As shown in FIGS. 5, 6 and 8, the slide carrier pickup and transfer mechanism 44 has a pair of blocks 244 and 246 each having a groove 248 therethrough, providing a track into which the base plate 130 of a slide carrier 34 releasably retained by a magnetic holder 110 of conveyor assembly 36 is inserted (FIG. 8) as the magnetic holder moves past the transfer mechanism. As the magnetic holder 110 goes past the pickup and transfer mechanism 44, the slide carrier 34 is initially inserted into the transfer mechanism and then the magnetic holder 110 is disconnected and separated from the slide carrier as the magnetic holder is moved by conveyor 36 in an arcuate path upwardly and around the sprocket 78. Blocks 244 and 246 are secured in opposed and spaced apart relation by screws 250 to a mounting bracket 252 fastened by screws 254 to bracket 56.

As successive slide carriers are moved by conveyor 36 into pickup and transfer mechanism 44, the slide carriers previously received in the transfer mechanism are pushed onto the drying rack and storage assembly 42 which has two loops of rigid wire 256 and 258, providing rails on which the carriers are retained as shown in FIG. 3. One end of each wire 256 and 258 is pressed into a blind hole in its associated block 244 and 246 and the other end of each wire is pressed into a blind hole in a mounting block 260 which is secured by a screw 262 to a dog leg bracket 264 fixed by a screw 266 to base 46.

As shown in FIG. 3, a uniform lateral spacing is maintained between wires 256 and 258 by a plurality of pairs of L shaped brackets 268 fixed to the undersides of the wires and rigidly interconnected by spacer rods 270.

To permit during operation of machine 32 attachment of slide carriers 34 to holders 110 of conveyor assembly 36, and also to permit liquid plastic coating material 142 to drain from slide plates 22 after they have passed through dip tank 38, drive motor 216 is turned off or pauses for about 10 seconds with the magnetic holders 110 in the position shown in FIG. 5 before each magnetic holder passes over absorber assembly 40. Drive motor 216 is switched on and off to provide this pause by an electric control relay 272 (FIG. 7) mounted by cap screws 274 on base 46 and electrically connected to drive motor 216. Electric power is supplied to relay 272 and hence drive motor 216 through a service cord 276 (FIG. 3), a fuse received in a fuse holder 278, and a master power switch 280 both of which are mounted on control panel 48. Electric power is also supplied to the drive motor 156 for the stirrer of tank assembly 38 through a rheostat 282 and an on-off switch 284 connected to the output side of master switch 280. Rheostat 282 and switch 284 are mounted on control panel 48 and permit the stirrer of tank assembly 38 to be turned on and off and the speed thereof varied.

In using machine 32 to carry out the process to produce microscope slides 20, cover 58 is swung fully open so that it rests on top of service panel 60, dip tank 140 is filled to the appropriate level with a liquid mixture 142 of a suitable plastic material and a compatible solvent for producing coating 26 on a slide plate 22, and the bath tray 180 of absorber assembly 40 is filled to the appropriate level with a liquid solvent 178 of the plastic material of coating 26. Service cord 276 is plugged into an appropriate electrical outlet and master switch 280 is turned on to drive conveyor assembly 36 and absorber assembly 40. Switch 284 is turned on and rheostat 282 adjusted to drive propeller 152 of dip tank assembly 38 at the proper speed for maintaining a uniform viscosity throughout the liquid mixture 142 in tank 140. Carriers 34 are loaded with slide plates 22 by inserting the plates between the leaves 126 of the carriers. While conveyor assembly 36 is stopped due to the pause caused by relay 272, a loaded carrier 34 is connected to the empty magnetic holder 110 immediately adjacent the idler sprocket 92 at the extreme left hand end of machine 32 as shown in FIG. 5.

As each loaded slide carrier 34 is intermittently advanced to the right in FIG. 5 by conveyor 36, it successively pauses before entering dip tank assembly 38, passes through dip tank assembly 38, pauses before passing over absorber assembly 40, passes over absorber assembly 40, pauses before entering pickup and transfer mechanism 44, and passes into pickup and transfer mechanism 44. As each slide carrier 34 passes through transfer mechanism 44, it is released while therein from its associated holder 110 of conveyor assembly 36, pauses in transfer mechanism 44, and is subsequently pushed on to storage and drying rack 42 by other slide carriers 34 subsequently entering pickup and transfer mechanism 44.

As each slide plate 22 passes through dip tank 140, it is partially submerged in liquid 142 to apply coating 26 in liquid form to the slide plate, and when the slide plate pauses before passing across absorber 40, any excess liquid coating drains from and accumulates as a meniscus adjacent the lower edge or bottom of the slide plate.

As each slide plate passes across absorber assembly 40, its lower edge contacts the upper surface of belt 158, preferably saturated with solvent 178 from tray 180, which absorbs any excess liquid coating which has accumulated at the lower edge or bottom of each slide plate 22 and thereby prevents the completed slide 20 from having an excess thickness of solid coating 26 at the lower edge or bottom thereof after the liquid coating has been converted to solid form.

The liquid coating 26 on each plate 22 is converted to solid form, preferably by evaporation of the solvent at room temperature, after the slide plate passes across absorber assembly 40 and preferably while it is received on storage and drying rack 42. Preferably the particular plastic material and the solvent of liquid mixture 142 are selected so that coating 26 will be converted to solid form or become substantially fully hardened at room temperature and atmospheric conditions within about 40 minutes and preferably about 20 minutes after the slide plate 22 passes across absorber assembly 40. Preferably the liquid coating 26 sets up sufficiently before the slide plate is pushed on to the storage and drying rack 42 so that any dust or other particulate contaminants in the atmosphere surrounding machine 32 do not become adhered to the coating 26 during completion of solidification of the coating while the slide plate is received on the drying and storage rack 42.

In carrying out the process of this invention, a satisfactory material for forming coating 26 which can be applied in liquid form has been found to be a clear and transparent synthetic enamel and compatible aromatic solvents of xylene and toluene. Preferably the clear and transparent plastic material for coating 26 and the compatible aromatic solvent are selected and mixed in such proportions that after the liquid mixture is applied to a slide plate 22, it will solidify into a solid coating 26 by evaporation of the solvent at ordinary conditions of room temperature, atmospheric pressure and humidity in less than one hour. However, with liquid mixtures of certain types of plastic materials and compatible solvents, it may be desirable or even necessary to convert the liquid coating to solid form by heating the coating to a temperature above room temperature.

In use, the process and machine 32 have easily, economically and reliably produced microscope slides 20 which are substantially less expensive than and of superior quality to conventional microscope slides and processes. Microscope slides 20 decrease the amount of refocusing of a microscope required to view the specimens on the slides, hermetically seal the specimens and are believed to prevent discoloration and deterioration of the specimens even if the slides are stored for many years.

I claim:

1. A process of preparing a microscope slide without any separate cover plate consisting essentially of applying a specimen to a slide plate of a transparent solid material which is of substantially uniform thickness, applying over the specimen and to the slide plate a liquid coating of a transparent plastic material of a type which will adhere itself to the slide plate with the liquid coating encircling and overlying at least the entire specimen on the plate and an area on the plate immediately adjacent the specimen, and subsequently converting the liquid coating to a solid coating which has a substantially flat exterior surface and is continuous over at least the specimen on the plate, permanently adheres to the plate, and hermetically seals the specimen on the plate so as to provide a microscope slide which does not have a separate cover plate of a clear transparent material overlying the specimen and fixed to the slide plate.

2. The process of claim 1 wherein the coating of plastic material is insoluble in water and soluble in an organic solvent.

3. The process of claim 1 wherein the liquid coating is applied to the plate by dipping the plate into the liquid coating and also comprises the steps of subsequently suspending the plate in a generally vertical plane to permit any excess liquid coating to accumulate adjacent an edge of the plate, and contacting such edge of the plate with an absorbent material to remove any accumulation of excess liquid coating from the plate.

4. The process of claim 3 which also comprises the step of suspending the plate with liquid coating thereon in a generally vertical plane while converting the liquid coating into a solid coating.

5. The process of claim 3 wherein the liquid coating of plastic material comprises a liquid organic solvent and the liquid coating is converted to a solid coating by evaporating at least part of the organic solvent from the liquid coating on the plate.

6. The process of claim 3 wherein the liquid coating of plastic material comprises an evaporable liquid solvent, and also comprises the step of suspending the plate with the liquid coating thereon in a generally vertical plane while converting the liquid coating to a solid coating by evaporating at least part of the liquid solvent.

7. The process of claim 3 wherein the absorbent material is saturated with a substance which is a solvent of the coating of plastic material.

8. The process of claim 7 which also comprises the step of suspending the plate with the liquid coating thereon in a generally vertical plane while converting the liquid coating into a solid coating.

9. The process of claim 7 wherein the liquid coating of plastic material comprises an evaporable liquid solvent, and also comprises the step of suspending the plate with the liquid coating thereon in a generally vertical plane while converting the liquid coating to a solid coating by evaporating at least part of the liquid solvent.

* * * * *